United States Patent
Brunner et al.

(10) Patent No.: US 10,180,358 B2
(45) Date of Patent: Jan. 15, 2019

(54) METHOD AND DEVICE FOR THE PHOTOTHERMIC INVESTIGATION OF A SAMPLE

(71) Applicant: Netzsch-Gerätebau GmbH, Selb (DE)

(72) Inventors: Martin Brunner, Konradsreuth (DE); Marc-Antoine Thermitus, Burlington, MA (US)

(73) Assignee: Netzsch-Gerätebau GmbH, Selb (DE)

( * ) Notice: Subject to any disclaimer, the term of this patent is extended or adjusted under 35 U.S.C. 154(b) by 70 days.

(21) Appl. No.: 15/343,916

(22) Filed: Nov. 4, 2016

(65) Prior Publication Data
US 2017/0122810 A1    May 4, 2017

(30) Foreign Application Priority Data
Nov. 4, 2015 (DE) .................. 10 2015 118 856

(51) Int. Cl.
| | |
|---|---|
| *G01J 5/02* | (2006.01) |
| *G01N 25/18* | (2006.01) |
| *G01J 5/10* | (2006.01) |
| *G01N 25/00* | (2006.01) |

(52) U.S. Cl.
CPC .............. *G01J 5/025* (2013.01); *G01J 5/10* (2013.01); *G01N 25/00* (2013.01); *G01N 25/18* (2013.01)

(58) Field of Classification Search
CPC ........................................... G01J 5/025
See application file for complete search history.

(56) References Cited

U.S. PATENT DOCUMENTS

| | | | | |
|---|---|---|---|---|
| 4,620,104 A * | 10/1986 | Nordal | ............ | G01J 3/108 250/352 |
| 7,262,414 B1 * | 8/2007 | Carrieri | ............ | G01N 21/64 250/339.08 |
| 2008/0315119 A1 * | 12/2008 | Blackmore | ........ | G01N 21/6428 250/459.1 |
| 2011/0170095 A1 * | 7/2011 | Menard | ............ | G01N 21/65 356/301 |

(Continued)

FOREIGN PATENT DOCUMENTS

DE     102012106955 B4     4/2014

OTHER PUBLICATIONS

"LFA 447 Nano Flash" from Netzsch-Gerätebau GmbH, Selb, Germany (downloadable on Jul. 4, 2012 on the Internet at http://netzsch-thermal-Analysis.com/download/LFA_447_NanoFlash_D_1108_de_180.pdf) pp. 1-12.

*Primary Examiner* — Manuel L Barbee
*Assistant Examiner* — Raymond Nimox
(74) *Attorney, Agent, or Firm* — Whitmyer IP Group LLC (57) ABSTRACT

A method for photothermal investigation of a sample (P), including: irradiating a first side of the sample (P) with an electromagnetic excitation pulse; detecting a result of the excitation pulse of one of the first side opposite second side of the sample (P) emitted thermal radiation (26); evaluating the detected thermal radiation based on a range defined by the following equations model:

$\partial 2T/\partial x2 = 1/\alpha \times \partial T/\partial t$ for $0 < x < L$, $t > 0$ $k \times \partial T/\partial x - h \times T = E(t) + \eta' \times (T(0,t) - T(L,t))$ for $x = 0$, $t > 0$ $k \times \partial T/\partial x + h \times d = -\eta' \times (T(0,t) - T(L,t))$ for $x = L$, $t > 0$ $T(x,0) = 0$ for $t = 0$.

27 Claims, 6 Drawing Sheets

(56) References Cited

U.S. PATENT DOCUMENTS

| | | | |
|---|---|---|---|
| 2014/0036955 A1* | 2/2014 | Brunner | G01N 21/1717 |
| | | | 374/131 |
| 2014/0247456 A1* | 9/2014 | Horstmann | A61B 5/0073 |
| | | | 356/502 |
| 2015/0339830 A1* | 11/2015 | Heissenstein | G01N 25/72 |
| | | | 348/90 |
| 2016/0109393 A1* | 4/2016 | Mandelis | G01N 25/72 |
| | | | 73/606 |

* cited by examiner

METHOD AND DEVICE FOR THE PHOTOTHERMIC INVESTIGATION OF A SAMPLE

TECHNICAL FIELD

The invention at hand relates to a method and a device for the photothermic investigation of a sample.

BACKGROUND

A method and a device for the photothermic investigation of a sample are known, for example, from the brochure "LFA 447 Nano Flash" from Netzsch-Gerätebau GmbH, Selb, Germany (downloadable on Jul. 4, 2012 on the Internet at http://netzsch-thermal-analysis.com/download/LFA_447_NanoFlash_D_1108_de_180.pdf). The known device comprises:
- a sample chamber in the form of an electrically operated oven with a sample holder accommodated therein for the arrangement and temperature control of the sample,
- a xenon flash lamp as excitation source for generating an excitation beam directed onto a front side, which functions as an "excitation side", of the sample to be investigated, and
- an infrared detector for detecting thermal radiation emitted from a "detection side", here the rear side of the sample.

A device and a method for the photothermic investigation of a sample is known from DE 10 2012 106 955 B4. In the case of this prior art, provision is made between the sample holder and the detector for an adjustable detecting lens, which can be adjusted in such a manner for setting a desired field of vision of the detector on the sample surface.

Physical characteristics of the material of the sample, such as in particular the temperature conductivity thereof, as well as the heat conductivity thereof, can be determined by means of the known device. With the knowledge of the density of the respective material, the specific thermal capacity of the material can also be determined.

It is the operating principle of the known device to irradiate a first side ("front side") of the sample with a short electromagnetic excitation pulse by means of the excitation source, to then detect a thermal radiation emitted from a second side ("rear side") of the sample located opposite the first side (as a measure for the temperature on the second side), as a result of the excitation pulse, and to finally evaluate the detected thermal radiation on the basis of a physical-mathematical model, so as to determine the mentioned material parameters (as the corresponding model parameters, which are estimated in response to the equalizing calculation) by means of a mathematical equalizing calculation.

The ability to control the temperature of the sample chamber optionally provides for such measurements either at a predetermined certain sample temperature, or across a larger temperature range (in that the temperature is changed in small steps, e.g., and a corresponding plurality of individual measurements is carried out).

Such a photothermic investigation works well for opaque samples, that is, without a larger permeability of the sample material for the thermal radiation created on the surfaces or (also) in the interior of the sample, respectively.

However, the investigation of more or less transparent samples is problematic, because the models resulting from physical-mathematical considerations in this case become relatively complex, in particular include numerous model parameters, which must be estimated in the equalizing calculation, so that the accuracy of the determination of the material parameters, which are ultimately of interest, such as in particular temperature conductivity and/or heat conductivity, e.g., suffers from this.

SUMMARY

It is an object of the invention at hand to show a novel way for a photothermic investigation of a sample, by means of which a determination of thermal material parameters is also made possible in particular for the transparent samples with a relatively high accuracy.

According to the invention, this object is solved by a method according to the independent claims of the invention.

The method according to the invention for the photothermic investigation of a sample comprises the steps of:
a) Irradiating a first side of the sample with an electromagnetic excitation pulse,
b) Detecting a thermal radiation emitted from a second side of the sample located opposite the first side as a result of the excitation pulse,
c) Evaluating the detected thermal radiation on the basis of a model, which is defined by the following equations:

$$\partial^2 T/\partial x^2 = 1/\alpha \times \partial T/\partial t \text{ for } 0 < x < L,\ t > 0$$

$$k \times \partial T/\partial x - h \times T = -E(t) + \eta' \times (T(0,t) - T(L,t)) \text{ for } x=0,\ t>0$$

$$k \times \partial T/\partial x + h \times T = -\eta' \times (T(0,t) - T(L,t)) \text{ for } x=L,\ t>0$$

$$T(x,0) = 0 \text{ for } t=0,$$

wherein:
T identifies the (location and time-dependent) temperature of the sample,
L identifies the thickness of the sample,
x identifies the spatial coordinate viewed in thickness direction of the sample, with x=0 on the first side of the sample and x=L on the second side of the sample,
t identifies the time with t=0 at the time of the excitation pulse,
E(t) identifies the (time-dependent) irradiation current density of the excitation pulse,
$\alpha$ identifies the temperature conductivity of the sample,
k identifies the heat conductivity of the sample,
h identifies the heat transfer coefficient on the sample surfaces,
$\eta'$ identifies an "overall transparency factor",
wherein a mathematical equalizing calculation is carried out so as to estimate one or a plurality of the afore-mentioned parameters $\alpha$, k, h, $\eta'$ and/or parameters derived therefrom, such as in particular "h/k" or "L×h/k", e.g., respectively, of the model by means of a temporal progression of the temperature T(L,t) determined from the detected thermal radiation on the second side of the sample (if the sample thickness L is known, as estimation of "L×k/h" is equivalent to an estimation of "k/h").

The estimation of such parameters in the model is hereby synonymous with the determination of the corresponding parameters for the sample.

The method thus allows in particular the determination of the temperature conductivity ($\alpha$) and also the heat conductivity (k), if the specific thermal capacity ($c_p$) is also known, or has been measured by means of a reference, e.g., respectively. Preferably, at least one of the material parameters α and k is output (and/or stored) after the evaluation has been concluded.

It is to be noted with regard to this that it is known that the parameters α, k are linked to the density (p) and to the specific thermal capacity ($c_p$), which thus allows for a simultaneous determination of the parameters α and k in connection with the evaluation, when knowing the density (p) and the specific thermal capacity ($c_p$).

In a preferred embodiment, the parameters α, L×h/k and η' are estimated in response to the mathematical equalizing calculation.

The excitation coil, which serves to heat the first side of the sample, can be generated by means of a flash lamp or a laser, e.g. In a preferred embodiment, the excitation pulse is generated by means of a laser, which is operated in a pulsed manner.

Preferably, the excitation pulse is generated with a wavelength range of (or, in the case of a monochromatic generation, with a dominating wavelength in a range of, respectively) between 100 nm and 5 μm. In particular in response to the use of a laser, the excitation pulse can be provided with a wavelength in the range of between 700 nm and 2 μm, e.g. (e.g. np: glass laser: 1062 nm).

A short pulse duration (pulse width) of the excitation pulse is advantageous in general, for example less than 1 ms, in particular less than 0.5 ms. On the other hand, also with regard to reaching a pulse energy, which is not too small, a pulse duration of at least 100 ns is advantageous in general (in particular very short pulse durations, e.g. in the range of a few 10 ns can be reached with Q-switched lasers, e.g.).

The pulse energy (per excitation pulse) is preferably at least 1 J, in particular at least 5 J. On the other hand, a pulse energy of maximally 50 J, in particular of maximally 20 J, is sufficient in many cases of application.

In a preferred embodiment, the sample is arranged in a gas-tight environment during the measuring procedure (irradiation with the excitation pulse and detecting the emitted thermal radiation). A well-defined environment or environmental condition, respectively, either a rare gas atmosphere and/or an evacuated environment (vacuum), e.g., which is advantageous for the reproducibility of the measurement, can thus be created in an advantageous manner.

To detect the thermal radiation, prior art, which is known for this, can be used. In particular, an infrared detector of a type, which is known per se, can be used for this. Preferably, such an infrared detector is cooled (e.g. $LN_2$-cooled).

As already mentioned, the invention is in particular directed to the photothermic investigation of transparent samples. In this regard, provision can in particular be made for a sample, which has a transmission coefficient of at least 0.3, in particular of at least 0.4, at least one location in the wavelength interval of between 2 μm and 6 μm.

The invention is in particular suitable for the investigation of samples of a glass material.

The sample to be investigated is preferably plateletshaped, e.g. of rectangular or circular format, and preferably has a thickness, which his uniform when observed across the sample surface.

The special embodiments and further developments described here for the method according to the invention can analogously be used as embodiments or further developments, respectively, of the device according to the invention. Embodiments and further developments described for the device can analogously be provided as embodiments or further developments, respectively, of the method.

The invention will be described in more detail below by means of exemplary embodiments of photothermic investigations with reference to the enclosed drawings.

DETAILED DESCRIPTION

Figure 1:
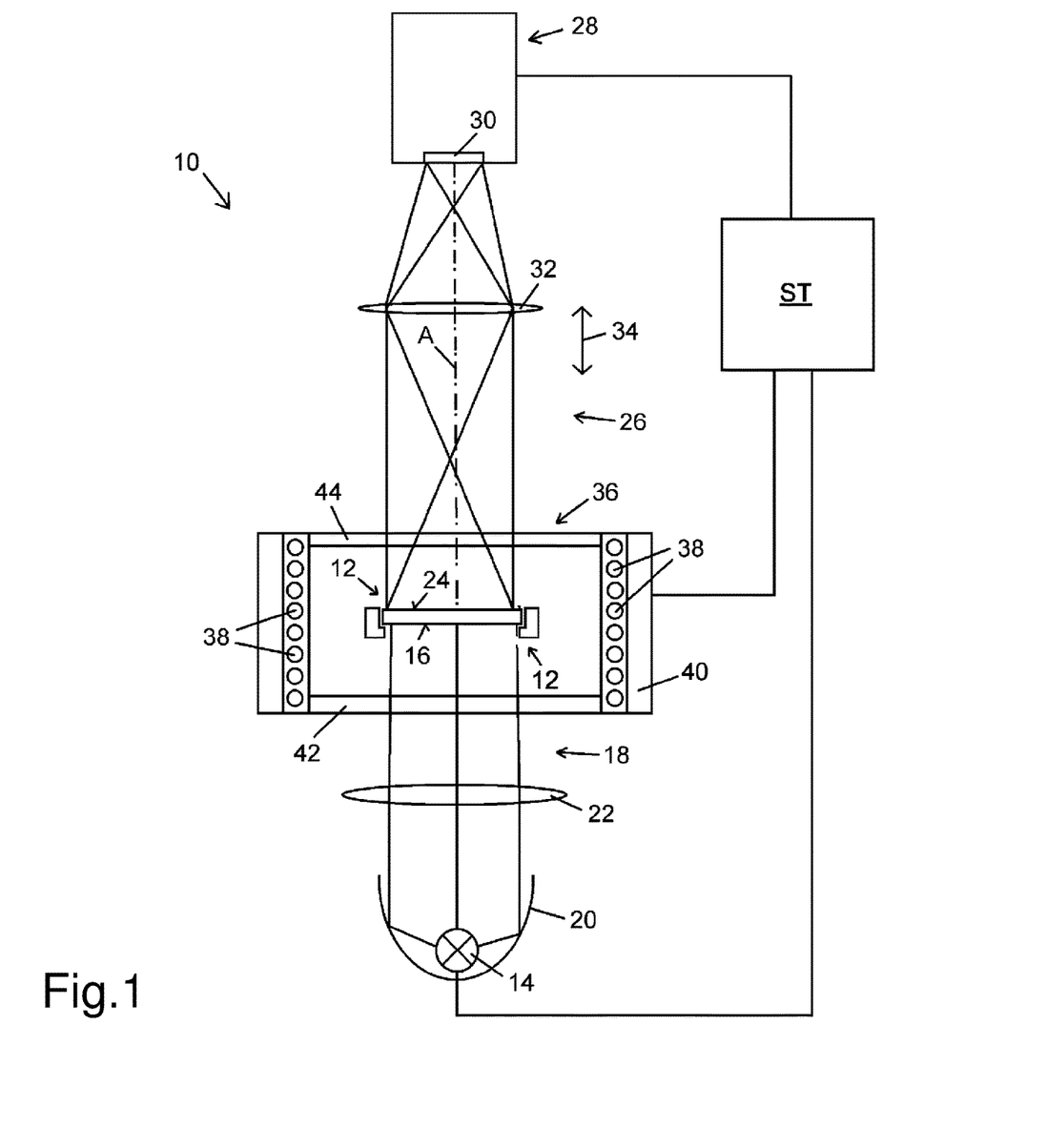
FIG. 1 shows a device for the photothermic investigation of a sample.

FIG. 1 shows, in a schematized manner, an exemplary embodiment of a device 10 for the photothermic investigation of a platelet-shaped (here cylindrical) sample P, which consists of a homogenous material and which is accommodated in a sample accommodation of a sample holder 12 of the device 10.

The device 10 further comprises a high-performance xenon flash lamp 14, which is operated in a pulsed manner, as an excitation source for generating electromagnetic excitation (radiation) pulses 18, which are directed onto a first side of the sample P, hereinafter also identified as "front side" 16 of the sample P.

As an alternative to a flash lamp, in particular a laser, which is operated in a pulsed manner, e.g., can be used as excitation source.

The energy of the individual excitation pulses 18 is approximately 10 J, e.g., and can be set by the user on a program-controlled control device ST.

The control device ST controls the operation of all of the controllable components of the device 10 in the context of selectable measuring programs.

In the illustrated example, the pulsed excitation beam 18 is directed onto the sample front side 16, which functions as "excitation side", by means of a reflector 20 and a collimation or focusing lens 22, respectively, wherein virtually the entire surface of the sample front side 16 is irradiated evenly in the illustrated example (see flash light beams illustrated in FIG. 1.)

The "excitation lens" in the illustrated exemplary embodiment, thus the lens 22, e.g., can optionally be provided as being adjustable, so that a setting of the area, which is to be irradiated with the excitation beam, can be made on the excitation side of the sample P (setting a "spot").

The individual heating pulses (excitation pulses 18) of the flash lamp 14 cause a time-dependent (here: pulsed) heating of the sample front side 16, so that, based on this, a heat pulse expansion through the material of the sample P all the way to a second side, which is located opposite the first side (front side), hereinafter also identified as "sample rear side" 24, results.

To detect the thermal radiation 26 emitted by the sample rear side 24, provision is made in the illustrated example for a (preferably cooled) infrared detector 28 comprising a radiation-sensitive detector area 30, wherein provision is made between the sample holder 13 and the detector 28 or the detector surface 30 thereof, respectively, for a detecting lens comprising a lens 32, which serves to define a desired, preferably circular "field of vision" of the detector 28 on the sample rear side 24.

The detecting lens can optionally be embodied for an adjustability of the field of vision on the sample rear side. In the illustrated example, provision can be made for this purpose for a displaceability of the lens 32 in the direction of an optical axis A, e.g. Such a displaceability of the lens 32 is symbolized in FIG. 1 by means of a double arrow 34.

With the knowledge (e.g. on the basis of the control) or by detecting (e.g. on the basis of a measurement), respectively, of a thermal energy input Q, which occurs by means of an excitation pulse 18 on the sample front side 16, and/or the temporal progression of an irradiation current density E(t) of the excitation pulse 18, an investigation ("photothermic investigation") of physical characteristics (material parameters) of the sample P can be realized in a manner, which will be described in more detail below, by means of a detection of the thermal radiation 26 emitted on the rear side 24 of the sample P.

Physical characteristics of the respective sample material determined by means of this investigation method are in particular the heat conductivity thereof as well as the temperature conductivity thereof (often also identified as "thermal diffusivity").

In the case of a preferred method alternative, the electromagnetic excitation on the sample front side as well as the thermal radiation detection on the sample rear side in each case takes place via substantially the entire front side or rear side, respectively, of the sample P. The heat conductivity and/or the temperature conductivity of a sample of homogeneous material can thus be determined accurately.

The "heat conductivity", hereinafter also identified with the symbol "k", quantifies the heat transport as a result of a temperature drop. Concretely, the heat conductivity corresponds to that heat quantity (in Joule, J. or Watt second, Ws, respectively), which flows through a 1 m thick material layer of the surface 1 m² within a time period of 1 s, when the temperature difference is 1 K.

The "temperature conductivity", hereinafter also identified with the symbol "$\alpha$", quantifies the temporal change of the spatial distribution of the temperature by means of heat conduction as a result of a temperature drop.

It is well-known that the following connection exists between these two material parameters k, $\alpha$:

$$k = \alpha \times p \times c_p.$$

k hereby identifies the heat conductivity
$\alpha$ hereby identifies the temperature conductivity
p hereby identifies the density
$c_p$ hereby identifies the specific thermal capacity To provide for a temperature-dependent determination of the material parameters k and/or $\alpha$, a jacket of a sample chamber 36, which includes the sample holder 12, comprises electrically operated heating elements 38 and optionally a cooling passage 40, through which a cooling agent can flow in a controlled manner, in the illustrated example of the device 10. A plurality of different sample temperatures can thus be set successively, e.g. in the context of a measuring program (or a temperature control can take place by means of a continuous heating or cooling, respectively), so as to in each case direct one or a plurality of excitation pulses onto the sample P for different sample temperatures, and so as to evaluate the intensity of the thermal radiation 26 detected thereupon for each excitation pulse for these different sample temperatures, and so as to thus also determine the temperature dependence of the material parameters k and/or $\alpha$.

The control device ST can be equipped (or connected) with suitable evaluating means (e.g. program-controlled computer unit) and display and/or storage means for outputting or storing, respectively, the determined material parameters.

In the illustrated example, frontal ends of the sample chamber 36 are formed by optical filters 42 (on the excitation side) and 44 (on the detection side). The filter characteristics thereof are provided in such a manner that a transmission is in each case only at hand for the spectral range, which is to be expected, if possible, thus for the spectrum of the excitation beam 18 (filter 42) on the one hand and for the spectrum of the thermal radiation 26 (filter 44) on the other hand.

To better understand the mode of operation of the device 10 according to the invention, evaluations, which initially are not within the scope of the invention but which are obvious for physical considerations, will be described below for the case of an "opaque sample P" (for the excitation radiation) and a "transparent sample P" (for the excitation radiation). This evaluation can be carried out, e.g., by means of the described device 10 (or with the control device ST included therein, respectively).

In the case of an opaque sample P, the model, which is defined by the following equations, is suitable for evaluating the intensity of the detected thermal radiation:

$$\alpha^2 T/\alpha x^2 = 1/\alpha \times \alpha T/\alpha t \text{ for } 0<x<L, t>0 \text{ (heat diffusion equation)} \quad (1)$$

$$k \times \alpha T/\alpha x - h \times T = -E(t) \text{ for } x=0, t>0 \text{ (boundary condition front side)} \quad (2)$$

$$k \times \alpha T/\alpha x + h \times T = 0 \text{ for } x=L, t>0 \text{ (boundary condition rear side)} \quad (3)$$

$$T(x,0)=0 \text{ for } t=0 \text{ (initial condition)} \quad (4)$$

wherein
T identifies the (location and time-dependent) temperature of the sample,
L identifies the thickness of the sample,
x identifies the spatial coordinate viewed in thickness direction of the sample, with x=0 on the front side of the sample and x=L on the rear side of the sample,
t identifies the time with t=0 at the time of the excitation pulse,
E(t) identifies the (time-dependent) irradiation current density of the excitation pulse,
$\alpha$ identifies the temperature conductivity of the sample,
k identifies the heat conductivity of the sample,
h identifies the heat transfer coefficient on the sample surfaces, In this model, the heat transfer coefficient h quantifies the (convective) heat loss on the respective sample side into the environment (in the sample chamber).

In the context of a measuring program carried out by means of the device 10, the control device ST controls the operation of the temperature-control means (heating elements 38 and cooling passage 40: e.g. "temporal temperature progression program") and the operation of the excitation source (xenon flash lamp 14 or laser, respectively: e.g. temporal pulse period and/or pulse energy), wherein, starting at the IR detector 28 as illustrated in FIG. 1, signals or data, respectively, which are representative of the temporal progression of the temperature T (L, t) on the sample rear side, or from which the control device can determine this temporal progression of the temperature T(L,t), are furthermore transferred to the control device ST.

Based on the above-described model, a mathematical compensating equation can thus be carried out by means of the control device ST, preferably in a program-controlled manner, so as to estimate in particular the parameters α and k of the model by means of a temporal progression of the temperature T(L,t) determined from the detected thermal radiation, on the sample rear side. These estimated parameters α and k are then the material parameters "heat conductivity" (also: "thermal conductivity") and "temperature conductivity (also "thermal diffusivity") of the respective sample P obtained by means of the evaluation.

This procedure will be illustrated once again below by means of an opaque (e.g. metallic) sample P using the example of a use of the device 10 with reference to a measuring result shown in FIG. 2.

Figure 2:
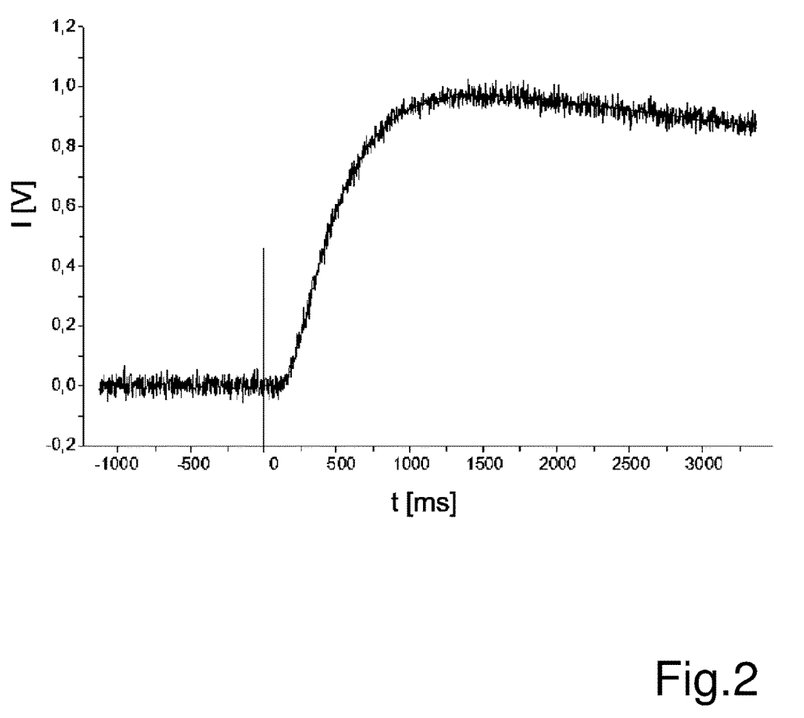
FIG. 2 shows a diagram of an exemplary progression of a thermal radiation detected in response to an investigation of an opaque sample as a function of the time.

FIG. 2 shows the temporal progression of a detector signal I, which is representative of a thermal radiation 26 detected by means of the detector 28 in an exemplary manner for an opaque sample P. For the sake of simplicity, it is assumed that this time-dependent progression l(t) is simultaneously representative of the temporal progression of the temperature T(L,t) on the rear side 24 of the sample P. In general, a corresponding conversion of the directly accommodated size l(t) into the size T(L,t), which is required for the subsequent further evaluation, can always be made in a suitable manner by means of the control device ST with the knowledge of the characteristics of the detector 28.

The irradiation of the sample front side by means of an excitation pulse 18 of predetermined energy and/or predetermined temporal progression of the irradiation current density E(t) takes place in FIG. 2 at a point in time t=0.

In the case of the sample P, which is opaque, that is, impermeable for thermal radiation, a heat input Q on the sample front side resulting from the irradiation corresponds to the integral of the irradiation current density E(t) of the excitation pulse 18 over the time t, multiplied by the irradiation surface.

In practice, the time period (temporal "width") of the excitation pulse 18 is mostly (and preferably) very much smaller than that time period, in which a temperature variation, which is characteristic depending on the sample thickness (L) and sample characteristics (in particular α and k), results subsequently on the sample rear side 24.

It is sufficient in this case, when only the total energy of the excitation pulse 18 (e.g. approx. 10 J) is known, e.g. The temporal progression of the irradiation current density E(t) can then be approximated or assumed mathematically, respectively, e.g. as Dirac's delta function δ(t): E(t)=Q/A_p× δ(t), wherein A_p identifies the surface irradiated by the excitation pulse.

As can be seen from FIG. 2, a rise of the temperature T(L,t) starts at a point in time of approximately t=130 ms on the sample rear side 24. This means concretely that the thermal energy Q input on the sample front side 16 "arrives" on the sample rear side 24 after approximately 130 ms.

At a point in time of approximately t=1500 ms, the temperature T(L,t) runs through a maximum. This means concretely that more heat "is lost" into the environment as of this point in time on the sample rear side 24 due to convection and/or irradiation than is (still) delivered additionally through the sample interior by means of convection.

It is clear that the mentioned points in time, but also the entire detailed progression of the variation of the temperature T(L,t) on the sample rear side 24 depend in particular on the material parameters α and k (or h/k, respectively) and can be described by the above-specified model, so that the parameters α and h/k of the model can readily be estimated by means of the mentioned mathematical equalizing calculation by means of the determined temporal progression of the temperature T(L,t) (e.g. mathematical "fit" of the parameters α and h/k (or L×h/k), respectively) by means of the "least squares method" or the like). At least the temperature conductivity (α) and the parameter "h/k" or "L×h/k" can thus be determined (calculated). With the knowledge or measurement, respectively, of the specific thermal capacity ($c_p$), this also provides the heat conductivity (k) of the respective sample P, as already explained.

The above-described model of the opaque sample is able to provide relatively accurate values of the material parameters α and h/k (or L×h/k, respectively). Concretely, the model of the opaque sample as a whole, which consists of 4 equations, includes "only" 2 unknown parameters (α and h/k), which must be estimated by means of an equalizing calculation.

However, the above-explained evaluation model is not suitable in the case of a sample P, which is more or less transparent for thermal radiation, but needs to be modified. The following model follows from physical considerations.

$$\partial^2 T/\partial x^2 = 1/\alpha \times \partial T/\partial t \text{ for } 0<x<L, t>0 \qquad (1)$$

$$k\times\partial T/\partial x - h\times T = -E(t) + h\times\eta\times(T(0,t)-T(L,t)) \text{ for } x=0, t>0 \qquad (2)$$

$$k\times\partial T/\partial x + h\times T = -h\times\eta\times(T(0,t)-T(L,t)) \text{ for } x=L, t>0 \qquad (3)$$

$$T(x,0)=0 \text{ for } t=0, \qquad (4)$$

wherein:
T identifies the (location and time-dependent) temperature of the sample,
L identifies the thickness of the sample,
x identifies the spatial coordinate viewed in thickness direction of the sample, with x=0 on the front side of the sample and x=L on the rear side of the sample,
t identifies the time with t=0 at the time of the excitation pulse,
E(t) identifies the (time-dependent) irradiation current density of the excitation pulse,
α identifies the temperature conductivity of the sample,
k identifies the heat conductivity of the sample,
h identifies the heat transfer coefficient on the sample surfaces,
η identifies a (dimensionless) "transparency factor".

This model for a transparent sample has thus in each been modified (supplemented) (as compared to the model of the opaque sample) in the two boundary conditions on the sample sides by the term h×η×(T(0, t)−T(L,t)). This term or the transparent factor η, which is then included, respectively, characterizes the energy transport, which takes place as a result of the transparency of the sample P by means of thermal irradiation through the sample P from the front side 16 to the rear side 24, accordingly.

Based on this model for a transparent sample, a mathematical equalizing calculation can also be performed, so as to estimate the parameters α, k, h and η or at least the parameters α, h/k and η of the model, respectively, by means of the temporal progression of the temperature T(L,t) on the sample rear side 24. The estimated parameters α and k, which result from this and in consideration of a thermal capacity also measured by means of a reference, e.g., are then the material parameters heat conductivity (k) and temperature conductivity (α) of the respective sample P, which are obtained by means of the evaluation.

This procedure will be illustrated below using the example of a use of the device 10 with reference to a measuring result shown in FIG. 3 with a transparent sample P (e.g. of a glass material).

Figure 3:
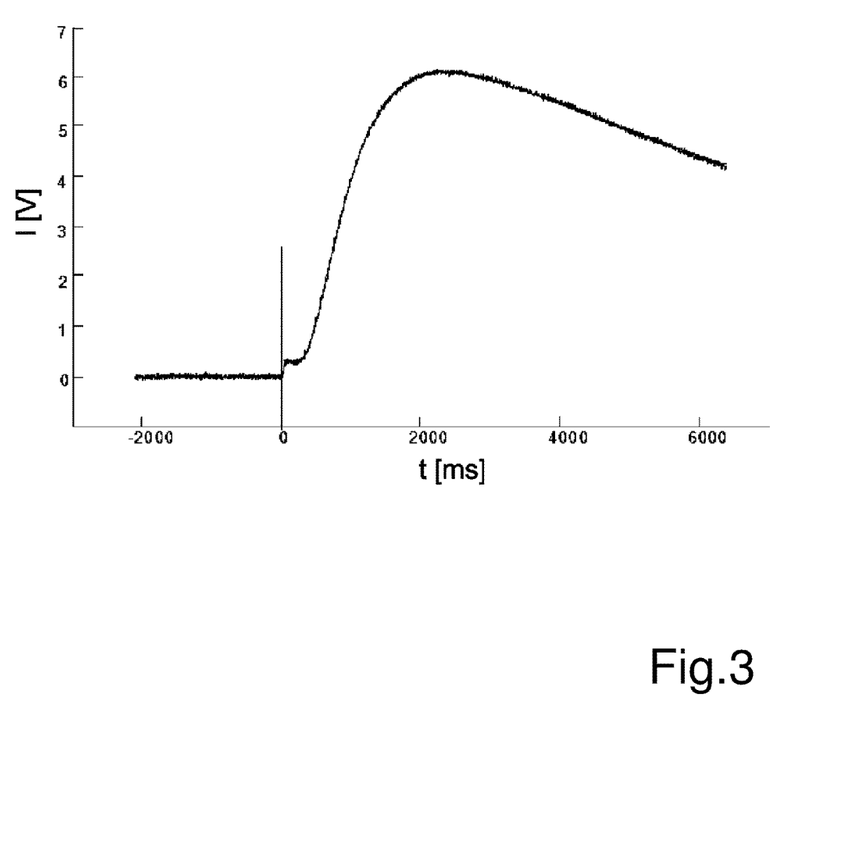
FIG. 3 shows a diagram of an exemplary progression of a thermal radiation detected in response to an investigation of a transparent sample as a function of the time, with relatively large losses of heat from the sample in the environment thereof.

FIG. 3 shows the temporal progression of a signal l, which is representative of an intensity of the thermal radiation 26 or the temporal progression of the temperature T(L,t), respectively, on the rear side 24 of the sample P.

The irradiation of the sample front side 16 with a short excitation pulse 18 of defined energy and/or predetermined temporal progression of the irradiation current density E(t) takes place a point in time t=0 in FIG. 3.

It shall be assumed, which is preferred, that the two sample sides 16, 24 are "blackened", so as to increase the absorption of the irradiation energy (on the front side 16) and the emission of the thermal radiation (on the rear side 24). In this case, a heat input Q on the sample front side, which results from the irradiation, again corresponds to the integral of the irradiation current density E(t) of the excitation pulse 18 over the time t, multiplied by the irradiation surface.

As can be seen from FIG. 3 and in contrast to the example according to FIG. 2, because the sample P is transparent, a small, gradual increase of the temperature T(L,t) at the sample rear side 24 begins almost immediately, thus with t=0 ms. This is so, because, starting at the sample front side 16, a certain energy portion passes through the sample P quickly due to thermal irradiation and increases the temperature T(L,t) on the rear side 24.

It can also be seen from FIG. 3, analogously to the example according to FIG. 2, that, after a certain delay (here in the magnitude of approximately 100 to 200 ms), the increase of the temperature T(L,t), which is effected by the heat conduction through the sample material, appears on the sample rear side 24 and becomes dominant subsequently.

At a point in time of approximately t=2280 ms in the illustrated example, the temperature T(L,t) runs through a maximum. Concretely, this means, in turn, that more heat "is lost" into the environment as of this point in time on the sample rear side due to convection and/or irradiation, than is delivered additionally through the sample interior.

The mentioned points in time, but also the entire temporal progression of the variation of the temperature T(L,t) on the sample rear side 24, are in particular dependent on the material parameters α, h/k (or L×h/k, respectively) and η, and can be described by the above-specified model.

The parameters α and K, and additionally the parameters h and η of the model could thus be estimated again by means of a mathematical equalizing calculation by means of the determined temporal progression of the temperature T(L,t), so as to determine the material parameters heat conductivity (k) and/or temperature conductivity (α) of the sample P.

It turned out, however, that it is not always possible with this model of the transparent sample to determine the material parameters k and a with sufficient accuracy (or with regard to the used method of the equalizing calculation with small "statistical uncertainty", respectively). Concretely, the reason for this might be that the model of the transparent sample, which consists of 4 equations, includes a total of 3 unknown parameters (to be estimated) (α, h/k and η), whereas the model of the opaque sample has one less unknown parameter (η) with the same number of equations.

It turned out in particular in this context that the model only "works" somewhat well, that is, provides sufficiently accurate values for k and a, when the temporal progression of T(L,t) actually (and as can be seen from FIG. 3, e.g.) passes through a rather clearly distinct maximum or if a more or less clear temperature decrease appears on the sample rear side towards the end of this progression, respectively.

This criterion is synonymous with the fact that "relatively high heat losses" into the environment (which are considered by the term h×η×(T(0,t)−T(L,t)) in the boundary conditions of the model) occur on the sample surfaces (or at least on the sample rear side 24, respectively).

Concretely, one explanation may be that a "high heat loss" or synonymously the corresponding decrease of the temperature T(L,t) towards the end advantageously increases the statistical reliability of the mathematical "fit" (equalizing calculation) with regard to the term "h×η", which is included in the boundary conditions.

In practice, however, it is advantageous in this regard on the other hand, when exactly these heat losses are minimized, because these losses are not necessarily detected completely exactly by the described model and because they are to furthermore be considered as being somewhat "disruptive" from a mathematical-physical aspect in response to the determination of the heat conductivity (k) and the temperature conductivity (α) of the sample P (due to the above-mentioned increase of the number of "unknowns").

The heat losses can in particular be reduced in that the measurement on the sample P is carried out under an evacuated environment, thus low pressure or vacuum, respectively, so as to reduce a heat conduction starting at the sample P into the environment accordingly. The device 10 is thus preferably equipped with (non-illustrated) means for evacuating the sample chamber 36. For example, these means can comprise, e.g., a vacuum pump, which is controlled by the control device ST and which is connected to the interior of the sample chamber 36.

According to the invention at hand, the device 10 is able to carry out a photothermal investigation of a transparent sample, even in response to relatively small heat losses of the mentioned type with relatively high accuracy of the determination of the respective material parameters at the same time, for instance based on a correspondingly selectable measuring program, which carries out a method according to the invention for the photothermal investigation of the sample.

The use of a novel model for describing the (transparent) sample in the context of the investigation method or in the context of the embodiment (e.g. programming), respectively, of the control device ST of the investigation device 10.

This novel model is defined by the following equations.

$$\partial^2 T/\partial x^2 = 1/\alpha \times \partial T/\partial t \text{ for } 0<x<L, t>0 \tag{1}$$

$$k \times \partial T/\partial x - h \times T = -E(t) + \eta' \times (T(0,t) - T(L,t)) \text{ for } x=0, t>0 \tag{2}$$

$$k \times \partial T/\partial x + h \times T = -\eta' \times (T(0,t) - T(L,t)) \text{ for } x=L, t>0 \tag{3}$$

$$T(x,0)=0 \text{ for } t=0 \tag{4}$$

wherein:
T identifies the (location and time-dependent) temperature of the sample, L identifies the thickness of the sample,
x identifies the spatial coordinate viewed in thickness direction of the sample, with x=0 on the first side of the sample and x=L on the second side of the sample,
t identifies the time with t=0 at the time of the excitation pulse,
E(t) identifies the (time-dependent) irradiation current density of the excitation pulse,
α identifies the temperature conductivity of the sample,
k identifies the heat conductivity of the sample,
h identifies the heat transfer coefficient on the sample surfaces,
η' identifies an "overall transparency factor".

Compared to the model explained above, which is "plausible" from a physical-mathematical view, the modification of the model, which is used according to the invention, is that the term h×η in the two boundary conditions has in each case been replaced by the new parameter T.

From a physical-mathematical view, an immediately obvious explanation does not result for the meaningfulness of this modification or the physical significance of the parameter η', respectively. In particular, the parameter η' can quasi be identified as a mere mathematical "auxiliary quantity" (without simply defined meaning from a physical aspect). On principle, the modification made according to the invention is obviously an oversimplification and thus a "deterioration" of the model.

When the control device ST carries out a mathematical equalizing calculation on the basis of this model, so as to estimate the parameters α, h/k (or L×h/k, respectively), η' of the model by means of the temporal progression of the temperature T(L,t), surprisingly accurate values can be determined therewith, in particular for the material parameters α and k, namely in particular advantageously also when "relatively small heat losses" into the environment take place on the sample surfaces 16, 24 in response to the sample investigation.

Figure 4:
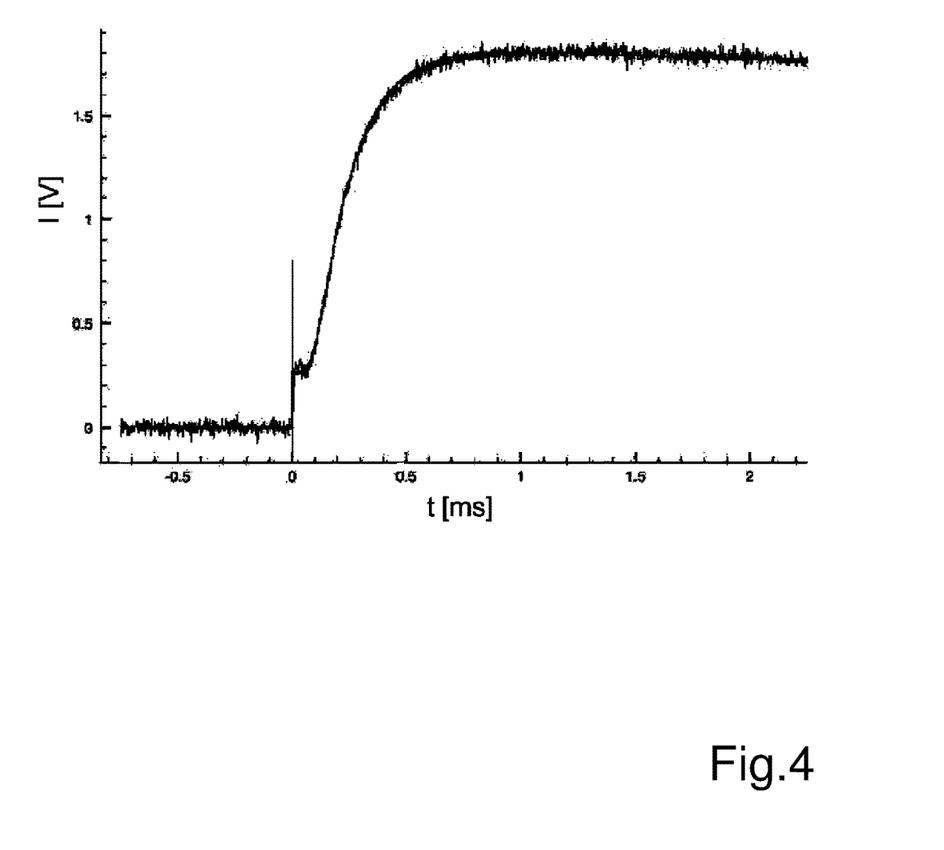
FIG. 4 shows a diagram of an exemplary progression of a thermal radiation detected in response to an investigation of a transparent sample as a function of the time, with relatively small losses of heat form the sample in the environment thereof.
Figure 5:
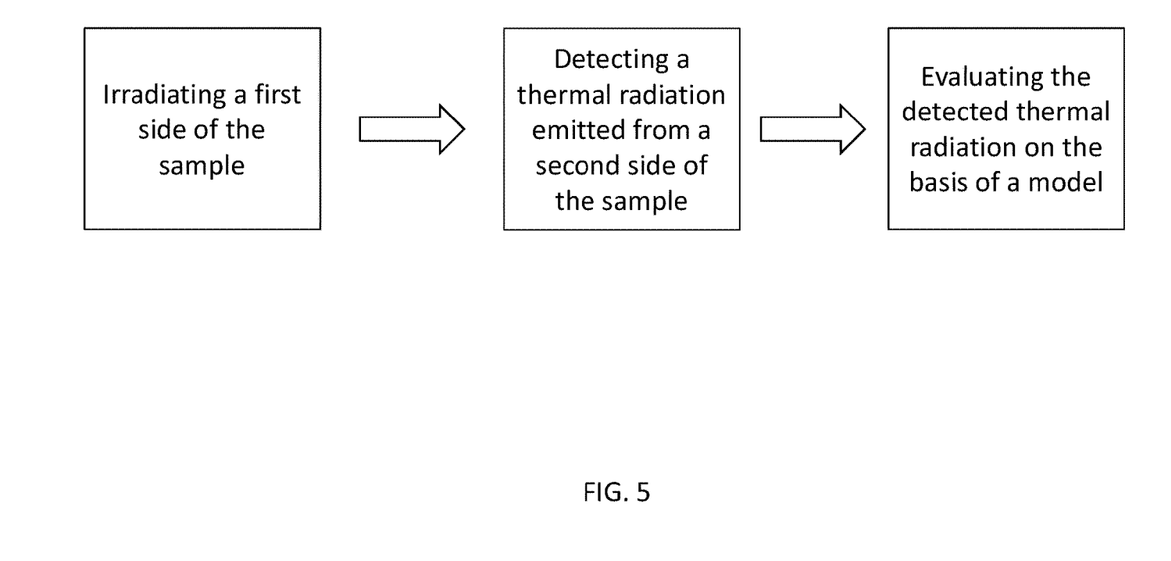
FIG. 5 shows a flowchart diagram of an embodiment of the process.
Figure 6:
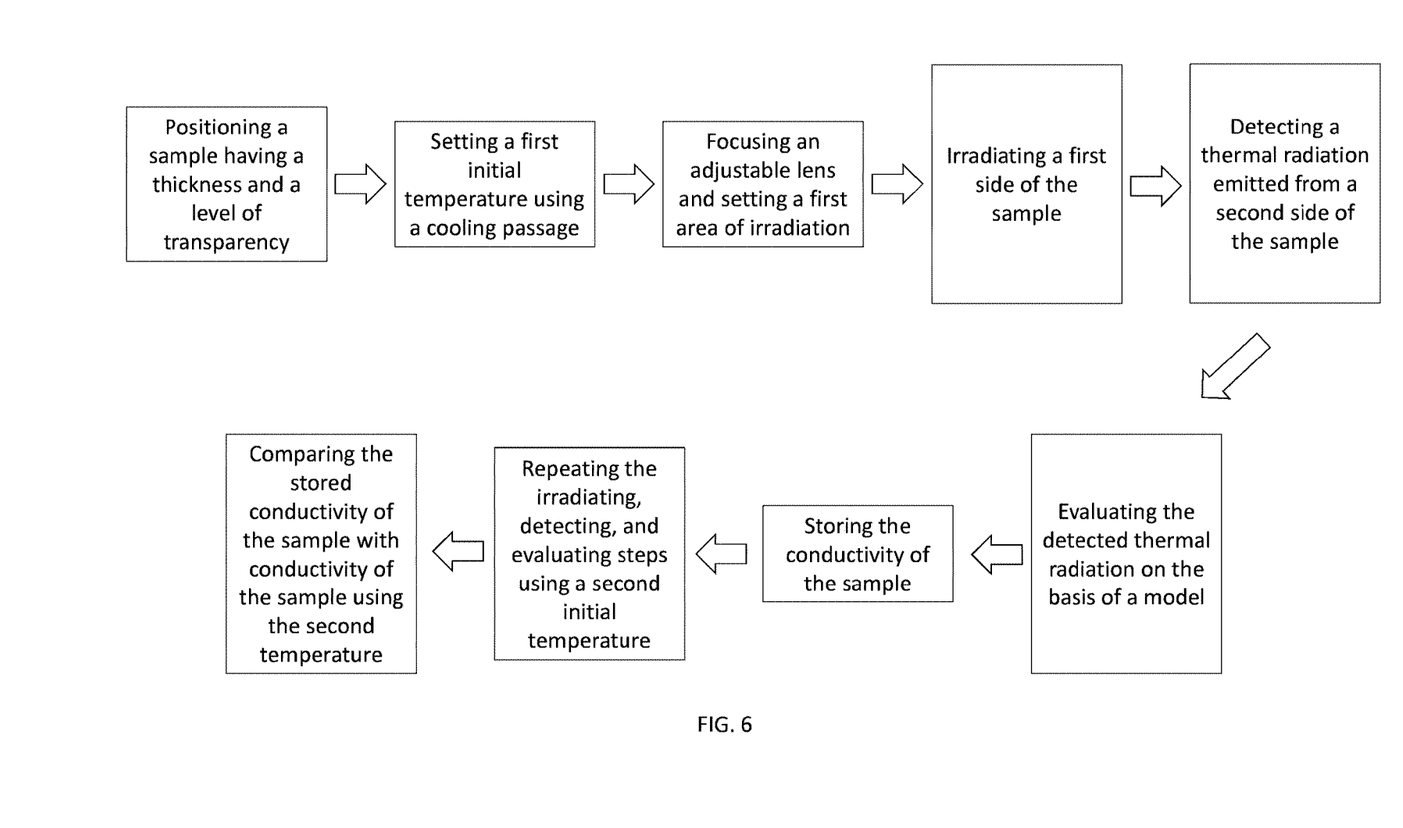
FIG. 6 shows a flow chart of a further embodiment of the process.

FIG. 4 shows the temporal progressions of a signal 1, which is representative of an intensity of the thermal radiation or the temporal progression of the temperature T(L,t), respectively, on the rear side 24 of the sample P in an exemplary manner for a transparent sample P, which is investigated under vacuum.

Due to the relatively low heat losses on the sample surfaces, the progression according to FIG. 4 differs from the progression according to FIG. 3 in that a distinct maximum is not passed through at the end of this progression. The strength of the novel model according to the invention, which also allows for the determination of relatively accurate values of the material parameters α and k at that point, is displayed in particular in such a case.

The invention claimed is:

1. A method for the photothermic investigation of a sample comprising the steps of:
   a) Irradiating a first side of the sample with an electromagnetic excitation pulse,
   b) Detecting a thermal radiation emitted from a second side of the sample located opposite the first side as a result of the excitation pulse,
   c) Evaluating the detected thermal radiation on the basis of a model, which is defined by the following equations:

$\alpha^2 T/\alpha x^2 = 1/\alpha \times \alpha T/\alpha t$ for $0<x<L$, $t>0$ $k\times\alpha T/\alpha x - h\times T = -E(t) + \eta'\times(T(0,t)-T(L,t))$ for $x=0$, $t>0$ $k\times\alpha T/\alpha x + h\times T = -\eta'\times(T(0,t)-T(L,t))$ for $x=L$, $t>0$ $T(x,0)=0$ for $t=0$, wherein:
T identifies the (location and time-dependent) temperature of the sample,
L identifies the thickness of the sample,
x identifies the spatial coordinate viewed in thickness direction of the sample, with x=0 on the first side of the sample and x=L on the second side of the sample,
t identifies the time with t=0 at the time of the excitation pulse,
E(t) identifies the (time-dependent) irradiation current density of the excitation pulse,
α identifies the temperature conductivity of the sample,
k identifies the heat conductivity of the sample,
h identifies the heat transfer coefficient on the sample surfaces,
η' identifies an "overall transparency factor",
wherein a mathematical equalizing calculation is carried out so as to estimate one or a plurality of the aforementioned parameters α, k, h, η' and/or parameters derived therefrom of the model by means of a temporal progression of the temperature determined from the detected thermal radiation on the second side of the sample.

2. The method according to claim 1, wherein the excitation pulse is generated by means of a flash lamp, which is operated in a pulsed manner.

3. The method according to claim 1, wherein the excitation pulse is generated with a wavelength of between 100 nm and 5 μm.

4. The method according to claim 1, wherein the sample is arranged in an evacuated environment during the irradiation of the first side with the excitation pulse and the detection of the thermal radiation of the sample emitted by the second side of the sample.

5. The method according to claim 1, wherein the detection of the emitted thermal radiation takes place by means of an infrared detector.

6. The method according to claim 1, wherein the sample has a transmission coefficient of at least 0.3, at least one location in the wavelength interval of between 2 μm and 6 μm.

7. The method according to claim 1, wherein the sample consists of a glass material.

8. A device for the photothermic investigation of a sample, comprising:
   an excitation source for irradiating a first side of the sample with an electromagnetic excitation pulse,
   a detector for detecting a thermal radiation emitted from a second side of the sample located opposite the first side as a result of the excitation pulse,
   an evaluating device, which is programmed to at least carry out an evaluation of the detected thermal radiation on the basis of a model, which is defined by the following equations:

$\alpha^2 T/\alpha x^2 = 1/\alpha \times \alpha T/\alpha t$ for $0<x<L$, $t>0$ $k\times\alpha T/\alpha x - h\times T = -E(t) + \eta'\times(T(0,t)-T(L,t))$ for $x=0$, $t>0$ $k\times\alpha T/\alpha x + h\times T = -\eta'\times(T(0,t)-T(L,t))$ for $x=L$, $t>0$ $T(x,0)=0$ for $t=0$, wherein:
T identifies the (location and time-dependent) temperature of the sample,
L identifies the thickness of the sample, x identifies the spatial coordinate viewed in thickness direction of the sample, with x=0 on the first side of the sample and x=L on the second side of the sample, t identifies the time with t=0 at the time of the excitation pulse, E(t) identifies the (time-dependent) irradiation current density of the excitation pulse, α identifies the temperature conductivity of the sample, k identifies the heat conductivity of the sample, h identifies the heat transfer coefficient on the sample surfaces, η' identifies an "overall transparency factor", wherein a mathematical equalizing calculation is carried out by means of the evaluating device so as to estimate one or a plurality of the afore-mentioned parameters a, k, h, η' and/or parameters derived therefrom of the model by means of a temporal progression of the temperature determined from the detected thermal radiation on the second side of the sample.

9. The device according to claim 8, further comprising a temperature-controllable sample chamber comprising a sample holder accommodated therein to arrange and temperature-control the sample.

10. The device according to claim 8, further comprising an adjustable excitation lens for setting a desired irradiation spot on the first side of the sample and/or an adjustable detecting lens for setting a desired field of vision of the detector on the second side of the sample.

11. The device according to claim 9, further comprising an adjustable excitation lens for setting a desired irradiation spot on the first side of the sample and/or an adjustable detecting lens for setting a desired field of vision of the detector on the second side of the sample.

12. The method according to claim 5, wherein the infrared detector is cooled.

13. The method according to claim 12, wherein the infrared detector is $LN_2$-cooled.

14. The method according to claim 3, wherein the excitation pulse is generated by means of a laser, which is operated in a pulsed manner, having a wavelength between about 700 nm and about 2 μm.

15. The device according to claim 8, wherein the excitation source is generated by means of a laser.

16. The device according to claim 15, the laser having a wavelength between about 100 nm and about 5 μm.

17. The device according to claim 15, the laser having a wavelength between about 700 nm and about 2 μm.

18. A device for determining conductivity of a sample comprising:
a temperature-controllable sample chamber comprising an adjustable sample holder accommodated therein to arrange and temperature-control the sample, and a cooling passage for controlling the temperature of the chamber;
a programmable excitation source, wherein the excitation source comprises a laser capable of producing pulse energy of between 5 Joules and 20 Joules per pulse, for irradiating a first side of the sample with an electromagnetic excitation pulse;
an adjustable lens for focusing the laser;
an IR detector for detecting a thermal radiation emitted from a second side of the sample located opposite the first side as a result of the excitation pulse,
an evaluating device, programmed to determine the conductivity of the sample by an evaluation of the detected thermal radiation on the basis of a model including a heat diffusion relationship, a boundary condition relationship for the first side, a boundary condition relationship for the second side.

19. The device according to claim 18, wherein the boundary condition relationship for the first side and the boundary condition relationship for the second side each include a characterization of energy transport from the first side to the second side.

20. The device according to claim 19, wherein the characterization of energy transport is directly related to a transparency factor of the sample.

21. The device according to claim 19, wherein the characterization of energy transport is directly related to a heat transfer coefficient of the first side of the sample and a heat transfer coefficient of the second side of the sample.

22. A method for the photothermic determination of conductivity of a sample comprising the steps of:
positioning a sample having a thickness and a level of transparency in a temperature-controllable sample chamber;
setting a first initial temperature using a cooling passage for the temperature-controllable sample chamber and the sample;
focusing an adjustable lens and setting a first area of irradiation;
irradiating the first area of irradiation of a first side of the sample for a period of time using a programmable excitation source, wherein the excitation source is a laser capable of producing pulse energy of between 5 Joules and 20 Joules per pulse;
detecting thermal radiation using a detector from a second side of the sample located opposite the first side as a result of the excitation pulse;
evaluating the conductivity of the sample using an evaluating device, programmed to determine the conductivity of the sample by an evaluation of the detected thermal radiation on the basis of a model including a heat diffusion relationship, a boundary condition relationship for the first side, a boundary condition relationship for the second side;
storing the conductivity of the sample;
repeating the irradiating, detecting, and evaluating steps using a second initial temperature of the temperature-controllable sample chamber and the sample or a second irradiation current density; and
comparing the stored conductivity of the sample with conductivity of the sample using the second temperature or second irradiation current density so as to determine temperature dependence of temperature conductivity and heat conductivity of the sample.

23. The method according to claim 22, wherein the boundary condition relationship for the first side and the boundary condition relationship for the second side each include a characterization of energy transport from the first side to the second side.

24. The method according to claim 23, wherein the characterization of energy transport is directly related to a transparency factor of the sample.

25. The method according to claim 23, wherein the characterization of energy transport is directly related to a heat transfer coefficient of the first side of the sample and a heat transfer coefficient of the second side of the sample.

26. The method according to claim 22, wherein the sample is translucent.

27. The method according to claim 1, wherein pulse durations are between about 100 ns and 0.5 ms.

* * * * *